United States Patent

Anderson

[11] Patent Number: 4,497,822
[45] Date of Patent: Feb. 5, 1985

[54] INSECTICIDAL N-BENZOYL-N'-PHENYL-N'-(R-THIO)UREAS

[75] Inventor: Martin Anderson, Whitstable, United Kingdom

[73] Assignee: Shell Oil Company, Houston, Tex.

[21] Appl. No.: 484,773

[22] Filed: Apr. 14, 1983

[30] Foreign Application Priority Data

Apr. 23, 1982 [GB] United Kingdom ............... 8211783

[51] Int. Cl.³ .................. C07C 83/10; A01N 37/18
[52] U.S. Cl. .......................... 514/592; 260/453 RW; 260/465 D
[58] Field of Search ............ 260/453 RW, 465 D; 424/298

[56] References Cited

U.S. PATENT DOCUMENTS 4,308,213 12/1981 Spatz et al. ............... 260/453 RW

Primary Examiner—Henry R. Jiles
Assistant Examiner—Robert C. Whittenbaugh

[57] ABSTRACT

Insecticidally active benzoylphenylurea derivatives of the formula:

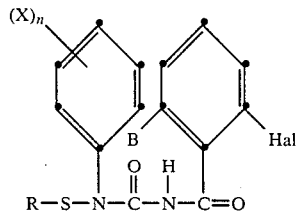

wherein R is haloalkyl, or phenyl optionally substituted by certain substituents and the other symbols have assigned meanings.

9 Claims, No Drawings

INSECTICIDAL N-BENZOYL-N'-PHENYL-N'-(R-THIO)UREAS

BACKGROUND OF THE INVENTION

For some time it has been known that certain N-benzoyl-N'-phenylureas are effective insecticides, but that they are difficult to apply in such a way as to attain that effectiveness in practice. To be effective, suchureas must be ingested by the insect, and it has been found that the smaller the particle(s) of insecticide ingested, the more effective the insecticide. In general, to attain the smallest size particles of a pesticide upon the foliage of a plant to be protected, it is desirable to apply a solution of the pesticide to the foliage. Ideally, this would be a solution in water. The ureas in question have very low solubility in water, so application of them in water solution is not feasible. Application of a solution of a pesticide in a solvent which is physically and economically suitable—such as xylene—is not ordinarily feasible because of the phytotoxicity of the solvent, when applied in the volume that could be needed under the circumstances. Therefore, it is common practice to formulate an essentially water-insoluble pesticide as an emulsible concentrate, in which the pesticide is in solution in an organic solvent that is physically and economically suitable—xylene is an example—which also contains one or more surface-active agents. Just prior to application to the plant, the concentrate is mixed with water, whereupon an emulsion forms, with very small droplets of the solution of pesticide being suspended in the water. When such an emulsion is applied to the plant, the organic solvent is not phytotoxic because of the small amount of it that is required, and evaporation of the solvent from the small droplets of solution provides the needed small particles of pesticide on the plant. To be suitable, physically, the solvent must be essentially insoluble in water, for otherwise it gradually passes into the water phase, leaving particles of pesticide, which precipitate, causing problems in application of the pesticide to the foliage of the plant, and retention of the particles of pesticide upon the foliage of the plant. To enable the use of an emulsible concentrate of the pesticide, the pesticide must have substantial solubility in the solvent. The ureas in question are only slightly soluble in such solvents, so application of such ureas as emulsible concentrates is not ordinarily feasible, and they are ordinarily applied as wettable powder formulations. It is more difficult to attain the needed particle size of the pesticide in such a case, requiring the use of sophisticated and expensive milling techniques.

DESCRIPTION OF THE INVENTION

A new class of N-benzoyl-N'-phenylureas has been discovered, the members of which are characterized by the high level of pesticidal activity of the known ureas, together with significantly increased solubility in solvents suitable for use in emulsible concentrate pesticide formulations, thus being more suited for use in such formulations.

The new ureas are N-benzoyl-N'-phenyl-N'-(R-thio)ureas of the formula:

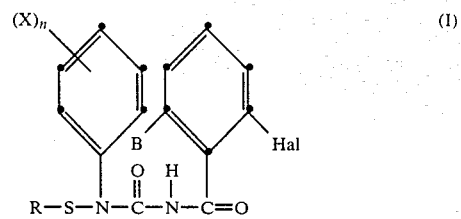

wherein Hal is a halogen atom; B is a hydrogen or halogen atom; X is halogen, cyano, haloalkyl, haloalkoxy, or phenoxy substituted by one or more of nitro, cyano, halogen, haloalkyl, and haloalkoxy; n is one, two or three; and R is haloalkyl, or phenyl optionally substituted by one or more of nitro, alkyl and halogen.

The halogen atom represented by "Hal" or by B may be fluorine, chlorine or bromine, but preferably is chlorine or fluorine.

The substituent X, or one of the substituents X, when n is two or three, preferably is bonded to the carbon atom in the 4-position of the ring, for compounds of Formula I containing this configuration appear to have superior pesticidal activity.

The haloalkyl or haloalkoxy moieties which X may represent preferably contain from one to six carbon atoms and from one to three halogen atoms, for example fluorine, chlorine or bromine, particular examples of such moieties being trifluoromethyl and trifluoromethoxy.

The phenoxy moiety which X can represent is preferably a nitrophenoxy, haloalkylphenoxy, haloalkoxyphenoxy, or haloalkyl-halophenoxy moiety in which the halogen atoms are fluorine, chlorine, or bromine and the alkyl and alkoxy moieties contain from one to four carbon atoms. Particular examples are the 2-chloro-4-trifluoromethylphenoxy and 4-nitrophenoxy moieties.

Preferably, R is haloalkyl of from one to six carbon atoms and from one to three fluorine, chlorine or bromine atoms, or is phenyl optionally substituted by one or more (suitably one or two) of nitro, alkyl of from one to six carbon atoms, fluorine, chlorine and bromine. Particularly useful compounds according to the invention are those in which R is phenyl substituted by at least one nitro moiety, preferably at the 2-position on the ring.

Preferred compounds of Formula I are those in which Hal is fluorine, chlorine or bromine; B is hydrogen, fluorine, chlorine or bromine; X is fluorine, chlorine, bromine, haloalkyl or haloalkoxy of from one to four carbon atoms and one to three fluorine, chlorine or bromine atoms, nitrophenoxy, haloalkylphenoxy, haloalkoxyphenoxy or haloalkyl-halophenoxy in which the halogen is fluorine, chlorine or bromine and the alkyl and alkoxy moiety contains from one to four carbon atoms; n is one, two or three, and R is haloalkyl of from one to six carbon atoms and one to three fluorine, chlorine or bromine atoms, or is phenyl optionally substituted by one or more of nitro, alkyl of from one to four carbon atoms, fluorine, chlorine and bromine.

Because of improved formulation characteristics and good pesticidal activity, the most preferred compounds of Formula I are those in which Hal is fluorine or chlorine; B is hydrogen, fluorine, or chlorine; X is chlorine, trifluoromethoxy, trifluoromethyl, 2-chloro-4-trifluoromethylphenoxy, or 4-nitrophenoxy, wherein X or one of X is bonded to the carbon atom at the 4-position in the ring; n is one, two or three; R is 2-nitrophenyl or 2,4-dinitrophenyl.

The compounds of Formula I may be prepared by a process which comprises reacting under anhydrous conditions a benzoylisocyanate of the formula:

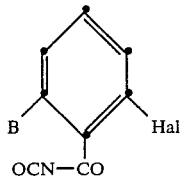

(II)

in which B and Hal have the meanings hereinbefore defined, with a sulphenamide of the formula

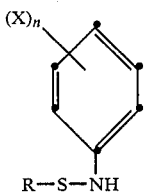

(III)

in which X, n and R have the meanings hereinbefore defined.

Preferably, the reaction is carried out in the presence of an aprotic solvent. Suitable solvents are aromatic solvents such as benzene, toluene, xylene, or chlorobenzene, hydrocarbons such as petroleum (b.p. 40°-60° C.), chlorinated hydrocarbons such as chloroform, methylene chloride or ethylene chloride, ethers such as diethylether, dibutylether, or dioxane.

Preferably, the reaction is carried out at a temperature in the range 0° to 100° C., suitably in the range 10° to 50° C. Preferably, the molar ratio of isocyanate to amine is from 1:1 to 2:1. The product may be worked up by the usual techniques. The starting materials of formulas III and IV are known compounds or may be prepared by methods analogous to those known in the art.

The compounds of the present invention have been found to have high pesticidal, for example insecticidal, activity. Accordingly, the present invention also provides pesticidal, particularly insecticidal, compositions comprising a compound of Formula I together with a carrier. Such a composition may contain a single compound or a mixture of several compounds of the invention. The invention further provides a method of combating pests, particularly insect pests, at a locus, which comprises applying an insecticidally effective amount of a compound or composition according to the present invention to a locus infested by or liable to infestation by pests.

The term "carrier" as used herein means an inert, horticulturally acceptable material (i.e., non-phytotoxic when applied to plants), that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminium silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compound of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

The surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols; encapsulated formulations and controlled release formulations are also contemplated, as are bait formulations. Wettable powders are usually compounded to contain 25, 50 or 75%w of toxicant and usually contain, in addition to solid carrier, 3–10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10%w of toxicant. Granules may be manufactured by extrusion of plastics, agglomeration or impregnation techniques. Generally, granules will contain 0.5–25%w toxicant and 0–10%w of additives such as stabilizers, slow release modifiers and binding agents. Emulsifiable concentrates usually contain, in addition to the solvent, and when necessary, cosolvent, 10-50%w/v toxicant, 2-20%w/v emulsifiers and 0-20%w/v of appropriate additives such as stabilizers, penetrants and corrosion inhibitors. Suspension concentrates are compounded so as to obtain a stable, nonsedimenting, flowable product and usually contain 10-75% toxicant, 0-5%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order of 0.01% to 0.5% based on the total weight of the formulation, though under some circumstances the effective concentration will be as little as 0.001% or as much as 2%, on the same basis.

The preparation, isolation and physical properties of typical individual species of the compounds of Formula I, in particular instances, are described in the following examples. In each case, the identity of the product, and each of any intermediate involved, was confirmed by appropriate chemical and spectral analyses.

The sulphenamide starting materials were prepared by a method based essentially on that of J. H. Billman, J. Garrison, R. Anderson, and B. Wolnak, *J. Amer. Chem. Soc.*, 1941, 63, p 1920.

EXAMPLE 1

2-Chloro-N-[[[4-(trifluoromethoxy)phenyl]-N-[(2-nitrophenyl)thio]amino]carbonyl]benzamide (1)

A solution of 50 g of 2-chlorobenzoyl isocyanate in 50 ml of dry toluene was added to a stirred solution of 60 g of N-[4-(trifluoromethoxy)phenyl]-2-nitrobenzenesulphenamide in 100 ml of the same solvent. The reaction was slightly exothermic, reaching a maximum temperature of 35° C. After 4 days at room temperature, the reaction mixture was cooled to −5° C. and the crystalline cake of product was broken up under cold toluene, filtered, washed with toluene followed by cold light petroleum (b.p. 40°-60° C.) and dried at 40° C. under reduced pressure, to give 1, as pale yellow crystals, m.p. 155°-158° C. (with decomposition).

EXAMPLE 2

2-Chloro-N-[[[4-(trifluoromethoxy)phenyl]-N-[(2,4-dinitrophenyl)thio]amino]carbonyl]benzamide (2)

A solution of 3.6 g of 2-chlorobenzoyl isocyanate in 20 ml of dry toluene was added to a stirred solution of 3.75 g of N-[4-(trifluoromethoxy)phenyl]-2,4-dinitrobenzenesulphenamide in 30 ml of the same solvent at room temperature. After 6 days, the reaction mixture was cooled to −5° C. and filtered, washed with cold toluene and with cold light petroleum (b.p. 40°-60° C.) to give 2, as pale yellow crystals, m.p.: 184°-186° C. (with decomposition).

EXAMPLE 3

N-[[[4-[(2-Chloro-4-(trifluoromethyl)phenoxy]phenyl]-N-[(2-nitrophenyl)thio]amino]carbonyl]-2,6-difluorobenzamide (3)

A solution of 1.0 g of 2,6-difluorobenzoyl isocyanate in 10 ml of dry methylene chloride was added over five minutes to a stirred solution of 2.2 g of N-[4-[2-chloro-4-(trifluoromethyl)phenoxy]phenyl]-2-nitrobenzenesulphenamide in 35 ml of the same solvent at room temperature. After 24 hours, the reaction mixture was diluted with dry light petroleum (b.p. 40°-60° C.) and the resulting precipitate of crude product was separated. Recrystallization of this material from ether/light petroleum gave 3, as pale yellow crystals, m.p.: 149°-152° C.

EXAMPLE 4

2-Chloro-N-[[[4-(trifluoromethoxy)phenyl]-N-[(2-methylphenyl)thio]amino]carbonyl]benzamide (4)

A solution of 2.0 g of 2-chlorobenzoyl isocyanate in 5 ml of dry toluene was added to a stirred suspension of 3.0 g of N-[4-(trifluoromethoxy)phenyl]-2-methyl-benzenesulphenamide in 40 ml of dry light petroleum at room temperature. After a few minutes, the reaction mixture became clear and subsequently the product came out of solution as an oil which eventually crystallized. After 24 hours the reaction mixture was cooled to −5° C. and filtered, and the pale purple product was washed with cold light petroluem. Recrystallization from ether/light petroleum gave 4, as colorless crystals, m.p.: 79°-80° C.

EXAMPLE 5

N-[[[4-Chlorophenyl]-N-[(2-nitrophenyl)thio]amino]carbonyl]-2,6-difluorobenzamide (5)

A solution of 1.8 g of 2,6-difluorobenzoyl isocyanate in 15 ml of dry toluene was added over 15 minutes to a stirred solution of 2.8 g of N-(4-chlorophenyl)-2-nitrobenzenesulphenamide in 35 ml of the same solvent at room temperature. After stirring overnight, the reaction was incomplete. A few drops of triethylamine were added, and after a further 24 hours, the reaction mixture was cooled to −5° C. and filtered, and the pale yellow product was washed with cold toluene. Traces of toluene were removed by drying under reduced pressure at about 40° C. for 3 days, to give 5, as a solid, m.p.: 176°-178° C.

EXAMPLE 6

2,6-Difluoro-N-[[[(trichloromethyl)thio]-N-[4-(trifluoromethyl)phenyl]amino]carbonyl]benzamide (6)

A solution of 2.0 g of 2,6-difluorobenzoyl isocyanate in 15 ml of dry methylene chloride was added to a stirred solution of 3.1 g of 1,1,1-trichloro-N-[4-(trifluoromethyl)phenyl]methanesulphenamide in 35 ml of the same solvent at room temperature. After 2 days, only partial reaction had occurred and 2.0 g of the isocyanate was added. After a total reaction time of 28 days, the reaction mixture was diluted with 400 ml of light petroleum (b.p. 40°-60° C.) and filtered. Evaporation of the solvent from the filtrate gave a residue from which 6 was obtained as colorless crystals, m.p.: 129°-130° C., by chromatography on silica gel using methylene chloride as eluent.

EXAMPLE 7

2-Chloro-N-[[[4-[2-chloro-4-(trifluoromethyl)phenoxy]phenyl]-N-[(trichloromethyl)thio]amino]carbonyl]benzamide (7)

A solution of 3.6 g of 2-chlorobenzoyl isocyanate in 15 ml of dry toluene was added over five minutes to a stirred solution of 4.0 g of 1,1,1-trichloro-N-[4-[2-chloro-4-(trifluoromethyl)phenoxy]phenyl]methanesulphenamide in 25 ml of the same solvent at room temperature. After 10 days, the reaction mixture was diluted with 500 ml of light petroleum andd filtered. Evaporation of the filtrate gave a crude residue from which 7 was obtained, as a solid. m.p: 68°-71° C., by rapid chromatography on silica gel using methylene chloride as eluent.

Further compounds of Formula I, listed in Table 1, following, were prepared according to procedures similar to those described above. In the table, the symbols are those of Formula I.

TABLE 1

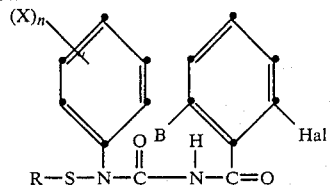

| Example No. | $(X)_n-$ | R | Hal | B | Melting Point (°C.) |
|---|---|---|---|---|---|
| 8 | 4-Cl— | $C_6H_5-$ | F | F | 115–117 |
| 9 | 4-Cl— | $2\text{-}CH_3-C_6H_4-$ | F | F | 125–128 |
| 10 | 4-Cl— | $3\text{-}CH_3-C_6H_4-$ | F | F | 140–142 |
| 11 | 4-Cl— | $4\text{-}CH_3-C_6H_4-$ | F | F | 130–133 |
| 12 | 4-Cl— | $4\text{-}Cl-C_6H_4-$ | F | F | 86–88 |
| 13 | 4-Cl— | $2,4(NO_2)_2-C_6H_3-$ | F | F | 171–173 |
| 14 | 4-Cl— | $Cl_3C-$ | F | F | 135–136 |
| 15 | $4\text{-}CF_3-$ | $C_6H_5-$ | F | F | 127–130 |
| 16 | $4\text{-}CF_3-$ | $2\text{-}CH_3-C_6H_4-$ | F | F | 120–123 |
| 17 | $4\text{-}CF_3-$ | $3\text{-}CH_3-C_6H_4-$ | F | F | 150–153 |
| 18 | $4\text{-}CF_3-$ | $4\text{-}CH_3-C_6H_4-$ | F | F | 142–145 |
| 19 | $4\text{-}CF_3-$ | $4\text{-}Br-C_6H_4-$ | F | F | 135–137 |
| 20 | $4\text{-}CF_3-$ | $2\text{-}NO_2-C_6H_4-$ | F | F | 115–118 |
| 21 | $4\text{-}CF_3-$ | $4\text{-}NO_2-C_6H_4-$ | F | F | 109–112 |
| 22 | $4\text{-}CF_3-$ | $2,4\text{-}(NO_2)_2-C_6H_3-$ | F | F | 143–145 |
| 23 | $4\text{-}CF_3O-$ | $4\text{-}CH_3-C_6H_4-$ | Cl | H | 124–126 |
| 24 | $4\text{-}CF_3O-$ | $4\text{-}NO_2-C_6H_4-$ | Cl | H | 177–178 |
| 25 | $4\text{-}CF_3O-$ | $Cl_3C-$ | Cl | H | 97–99 |
| 26 | $4\text{-}CF_3-$ | $4\text{-}t\text{-butyl-}C_6H_4-$ | F | F | 63–66 |
| 27 | $4\text{-}CF_3-$ | $4\text{-}Cl-C_6H_4-$ | F | F | 144–146 |
| 28 | 4-Cl— | $4\text{-}NO_2-C_6H_4-$ | F | F | 110–113 |
| 29 | $4\text{-}(2\text{-}Cl-4\text{-}CF_3-C_6H_3O)-$ | $C_6H_5-$ | Cl | H | 55–58 |
| 30 | " | $4\text{-}Cl-C_6H_4-$ | Cl | H | 93–95 |
| 31 | " | $2\text{-}CH_3-C_6H_4-$ | Cl | H | 65–68 |
| 32 | $4\text{-}CF_3O-$ | $2\text{-isopropyl-}C_6H_4-$ | Cl | H | 65–68 |
| 33 | $4\text{-}CF_3O-$ | $4\text{-}Cl-C_6H_4-$ | Cl | H | 124–126 |
| 34 | $4\text{-}(2\text{-}Cl-4\text{-}CF_3-C_6H_3O)-$ | $4\text{-}CH_3-C_6H_4-$ | Cl | H | 133–135 |
| 35 | $4\text{-}(2\text{-}Cl-4\text{-}CF_3-C_6H_3O)-$ | $2\text{-}NO_2-C_6H_4-$ | Cl | H | 136–138 |
| 36 | 4-Cl— | $4\text{-}t\text{-butyl-}C_6H_4-$ | F | F | 93–96 |
| 37 | 4-Cl— | $4\text{-}Br-C_6H_4-$ | F | F | 119–121 |
| 38 | $3,5\text{-}Cl_2-4\text{-}(4\text{-}NO_2-C_6H_4O)-$ | $2\text{-}NO_2-C_6H_4-$ | F | F | 126–129 |

EXAMPLE 39

The insecticidal activity of the compounds of the invention was determined in the following tests.

TEST 1

The insecticidal and ovicidal activities of the compounds of the invention were assessed employing the pests, Egyptian cotton leafworm (*Spodoptera littoralis*, S.l.), mosquito (*Aedes aegypti*, A.a.) and eggs of *Spodoptera littoralis*, S.l.ov.

The test methods used for each species are described below. In each case the tests were conducted under normal insectary conditions (28° C.±20° C.; fluctuating light and humidity).

In each instance, the toxicity of the compound of the invention was compared to that of a standard pesticide (parathion), its relative toxicity then being expressed in terms of the relationship between the amount of compound of the invention and the amount of the standard pesticide required to produce the same percentage (50%) of mortality in the test insect. By assigning the standard pesticide an arbitrary rating of 100, the toxicities of the compounds of the invention were expressed in terms of the toxicity indices, which compares the toxicity of the compounds of the invention with that of the standard pesticide. That is to say, a test compound having a Toxicity Index of 50 would be half as active, while one having a Toxicity Index of 200 would be twice as active as the standard pesticide. The Toxicity Indices are set forth in Table 2.

(a) *Spodoptera littoralis*—A solution or suspension of the test compound was made up over a range of concentrations in 10% acetone/water containing 0.025% Triton X100 (as surfactant). These solutions were sprayed using a logarithmic spraying machine onto petri dishes containing a nutritious diet on which the *Spodoptera littoralis* larvae had been reared. When the spray deposit had dried each dish was infested with 10 second instar larvae. Mortality assessments were made 7 days after spraying.

(b) *Aedes aegypti*—Several solutions of the test compound of varying concentration were prepared in acetone. 100 microliter quantities were added to 100 milliliters of tap water, the acetone being allowed to evaporate off. Ten early fourth instar larvae were placed in the test solution; after 48 hours the (surviving) larvae were fed with animal feed pellets, and the final percentage mortality assessed when all the larvae had either pupated and emerged as adults or died.

(c) *Spodoptera littoralis* (ovicide)—Solutions as described in (a) above were prepared. Eggs less than 24 hours old were obtained as follows. Adult *Spodoptera littoralis* were held in large plastic cylinders containing blotting paper on which the moths laid their batches of eggs. Egg batches containing approximately 60–70 eggs were cut from the blotting paper with a 1 cm surround. These were placed, eggs uppermost, on filter paper in the deeper half of 5 cm disposable petri dishes and each batch of eggs was then sprayed with a different test solution or the control solution. The dishes were covered until the control eggs had hatched, approximately five days. The percentage ovicidal mortality was then calculated.

TABLE 2

| Compound of Example | Toxicity Index | | |
|---|---|---|---|
| | S.l. | A.a. | S.l.ov. |
| 1 | 750 | 220 | 210 |
| 2 | 150 | 82 | 3300 |
| 3 | 4500 | — | 0 |
| 4 | 110 | 77 | 2200 |
| 5 | 90 | 220 | 0–4 |
| 6 | 260 | 34 | 400 |
| 7 | 1800 | 55 | 0 |
| 8 | 16 | 22 | 480 |
| 9 | 43 | 31 | 1400 |
| 10 | 20 | 24 | 1400 |
| 11 | 23 | 25 | 680 |
| 12 | 17 | 14 | — |
| 13 | 35 | 100 | 1800 |
| 14 | 10 | 6 | 560 |
| 15 | 170 | 50 | 1800 |
| 16 | 550 | — | 2700 |
| 17 | 260 | 160 | 2800 |
| 18 | 300 | 170 | 2300 |
| 19 | 240 | 10 | 1500 |
| 20 | 160 | 180 | 1800 |
| 21 | 96 | 13 | — |
| 22 | 220 | 51 | 2300 |
| 23 | 140 | 145 | 1500 |
| 24 | 54 | 31 | 11 |
| 25 | 140 | 28 | 1300 |
| 26 | 580 | 82 | 8 |
| 27 | 220 | 21 | 2200 |

TABLE 2-continued

| Compound of Example | Toxicity Index | | |
|---|---|---|---|
| | S.l. | A.a. | S.l.ov. |
| 28 | 54 | 6 | 720 |
| 29 | 930 | 330 | 0 |
| 30 | 670 | 220 | 0 |
| 31 | 960 | 240 | 0 |
| 32 | 88 | 28 | 2000 |
| 33 | 57 | 44 | 1300 |
| 34 | 1200 | 130 | 0 |
| 35 | 2500 | 82 | 0 |
| 36 | 42 | 22 | 0 |
| 37 | 51 | 26 | 850 |
| 38 | 330 | 30 | 0 |

EXAMPLE 40

To illustrate the improved solubility in a common formulation solvent, xylene, of the compounds according to the invention, solubility tests were carried out with certain of these compounds and closely related compounds known from the literature. The test method is described below.

The compound (200 mg) was equilibrated with solvent (0.5 ml of o-xylene at 20° C. in the dark for 48 hours). After equilibration, the supernatant liquors were removed, centrifuged and then filtered. An aliquot portion of this (0.1 ml) was made up to volume (1 to 100 ml) with acetonitrile and then analyzed against standards by means of liquid chromatography.

The results were as shown in the following table.

| SOLUBILITY RESULTS | |
|---|---|
| Compound | Solubility in Xylene (g/l) |
| Compound of Example 1 | 3.7 |
| 1-(4-trifluoromethoxy-phenyl)-3-(2-chloro-benzoyl)-urea (see German Patent Specification 2.601.780) | 2.3 |
| Compound of Example 3 | 18.8 |
| 1-(4-(4-trifluoromethyl-2-chlorophenoxy)phenyl)-3-(2,6-difluorobenzoyl)urea (see Belgian Patent 838.286) | 5.7 |

It can be seen that the compounds of Formula I are substantially more soluble in xylene than the known compounds, and hence more readily converted into manageable emulsible concentrate formulations.

I claim:

1. A compound of the formula:

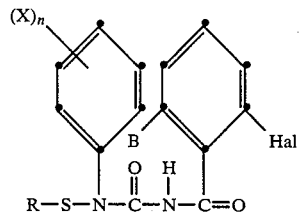

wherein Hal is a halogen atom; B is a hydrogen or halogen atom; X is halogen, cyano, lower haloalkyl, lower haloalkoxy, or phenoxy substituted by one or more of nitro, cyano, halogen, lower haloalkyl, and lower haloalkoxy; n is one, two or three; and R is lower haloalkyl, or phenyl optionally substituted by one or more of nitro, lower alkyl, and halogen.

2. A compound according to claim 1 wherein Hal is fluorine, chlorine or bromine; B is hydrogen, fluorine, chlorine or bromine; X is fluorine, chlorine, bromine, haloalkyl or haloalkoxy of from one to four carbon atoms and one to three fluorine, chlorine or bromine atoms, a nitrophenoxy, haloalkylphenoxy, haloalkoxyphenoxy or haloalkyl-halophenoxy moiety in which the halogen is fluorine, chlorine or bromine and the alkyl and alkoxy moiety each contains from one to four carbon atoms; n is one, two or three; and R is haloalkyl of from one to six carbon atoms and from one to three fluorine, chlorine or bromine atoms or is phenyl optionally substituted by one or more of nitro, alkyl of from one to four carbon atoms, fluorine, chlorine and bromine.

3. A compound according to claim 2 wherein Hal is fluorine or chlorine; B is hydrogen, fluorine or chlorine; X is chlorine, trifluoromethoxy, trifluoromethyl, 2-chloro-4-(trifluoromethyl)phenoxy or 4-nitrophenoxy wherein X or one of X is in the 4-position; n is one, two or three; R is 2-nitrophenyl or 2,4-dinitrophenyl.

4. A method for controlling insects at a locus which comprises applying to said locus an effective amount of a compound of claim 1.

5. A method for controlling insects at a locus which comprises applying to said locus an effective amount of a compound of claim 2.

6. A method for controlling insects at a locus which comprises applying to said locus an effective amount of a compound of claim 3.

7. A insecticidal composition comprising an effective amount of a compound of claim 1 together with a horticulturally acceptable carrier, and optionally a surface-active agent.

8. A insecticidal composition comprising an effective amount of a compound of claim 2 together with a horticulturally acceptable carrier, and optionally a surface-active agent.

9. A insecticidal composition comprising an effective amount of a compound of claim 3 together with a horticulturally acceptable carrier, and optionally a surface-active agent.

* * * * *